United States Patent
Ahtchi-Ali et al.

(10) Patent No.: US 6,963,004 B2
(45) Date of Patent: Nov. 8, 2005

(54) PROCESS FOR MAKING DIRECTLY ESTERIFIED FATTY ACID ISETHIONATE USING GROUP 4 METAL BASED, PARTICULARLY ZIRCONIUM BASED CATALYSTS

(75) Inventors: Badreddine Ahtchi-Ali, Martinsville, NJ (US); Natasha Pfeiffer Campbell, New York, NY (US); John Robert Winters, Dumont, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/744,745

(22) Filed: Dec. 23, 2003

(65) Prior Publication Data

US 2005/0137411 A1 Jun. 23, 2005

(51) Int. Cl.[7] ............................................. C07B 45/00
(52) U.S. Cl. ............................................................. 554/92
(58) Field of Search ............................................... 554/92

(56) References Cited

U.S. PATENT DOCUMENTS

| | | |
|---|---|---|
| 3,320,292 A | 5/1967 | Cahn et al. |
| 3,383,396 A | 5/1968 | Cahn et al. |
| 4,405,526 A | 9/1983 | Lamberti et al. |

OTHER PUBLICATIONS

International Search Report Application No. PCT/EP 2004/013957 mailed Apr. 15, 2005.

*Primary Examiner*—Deborah D. Carr
(74) *Attorney, Agent, or Firm*—Ronald A. Koatz

(57) ABSTRACT

The invention relates to a process for catalyzing a DEFI reaction using Group 4 metal based catalyst (according to IUPAC).

4 Claims, 2 Drawing Sheets

PROCESS FOR MAKING DIRECTLY ESTERIFIED FATTY ACID ISETHIONATE USING GROUP 4 METAL BASED, PARTICULARLY ZIRCONIUM BASED CATALYSTS

FIELD OF THE INVENTION

The invention relates to a process for catalyzing the preparation of directly esterified fatty acid isethionate (DEFI) using Group 4 based, particularly zirconium based catalysts. (Group 4 defined by "new" IUPAC format, previously known as Group IV A under previous IUPAC format, both formats being shown in the Periodic Table of Elements set forth in the CRC Handbook of Chemistry and Physics, $93^{rd}$ ed. 2002–2003, hereby incorporated by reference.)

BACKGROUND

Directly esterified fatty acyl isethionate (DEFI) is produced by the direct esterification of an alcohol of formula:

HOR'SO$_3$M with an organic acid (e.g. fatty acid) of formula:

RCOOH to produce a surface acting agent (i.e., DEFI) of formula:

RCOOR'SO$_3$M where R is a monovalent aliphatic hydrocarbon radical having 7 to 24, preferably 8 to 22 carbon atoms; R' comprises divalent aliphatic hydrocarbon radicals containing 2 to 4 carbons; and M is an alkali metal cation, particularly sodium, potassium or lithium; or an ammonium cation. In the reaction to make DEFI, the alcohol and organic acid noted above are reacted in the presence of a catalyst in order to accelerate and produce commercially viable yields.

Surface active agents are one of the basic raw materials in the detergent industry. Specifications for such materials generally require the absence of colored impurities in order to prepare high quality, aesthetically pleasant, formulated products such as detergent bars. Absence of colored impurities also minimizes the chances of imparting off-odors to formulated products. Thus, it is obviously desirable to use catalysts which do not cause color impurities when catalyzing the DEFI reaction. It is further desirable to use DEFI catalysts which provide good reaction rates as well as not leaving undesirable corrosivity toward stainless steel used in DEFI reactors.

U.S. Pat. No. 3,320,292 to Cahn et al. discloses catalysis of DEFI using zinc oxide, zinc soap or mixtures. Group 4 metal catalysts of the subject invention provide far superior reaction rates when used in comparable amounts with zinc oxide.

U.S. Pat. No. 4,405,526 to Lamberti discloses catalysis of DEFI using a mixture of zinc oxide and an organic sulfonic acid.

Unexpectedly, applicants have now found that Group 4 metal (defined by the well known Periodic Table of the Elements according to IUPAC convention, new notation) based compounds catalyze the reaction of DEFI faster and more cheaply compared to commercially known catalysts (e.g., zinc oxide). Further, the reaction with these catalysts do not lead to corrosion or color disfiguration problems at catalytic levels. Using these catalysts, it is thus possible to enhance reaction kinetics, increase production capacity of DEFI and reduce manufacturing costs.

BRIEF DESCRIPTION OF THE INVENTION

Specifically, the subject invention relates to a process for producing DEFI which comprises reacting a fatty acid with an alkali metal isethionate or ammonium isethionate in the presence of a catalyst comprising a group 4 metal. The process is based essentially on commercial processes wherein ingredients are heated to a temperature of about 190° to 255° C. for sufficient time to produce DEFI. Catalysts comprising any Group 4 metal compound may be used although those comprising a zirconium or hafnium compound are particularly preferred.

DETAILED DESCRIPTION OF THE INVENTION

Figure 1:
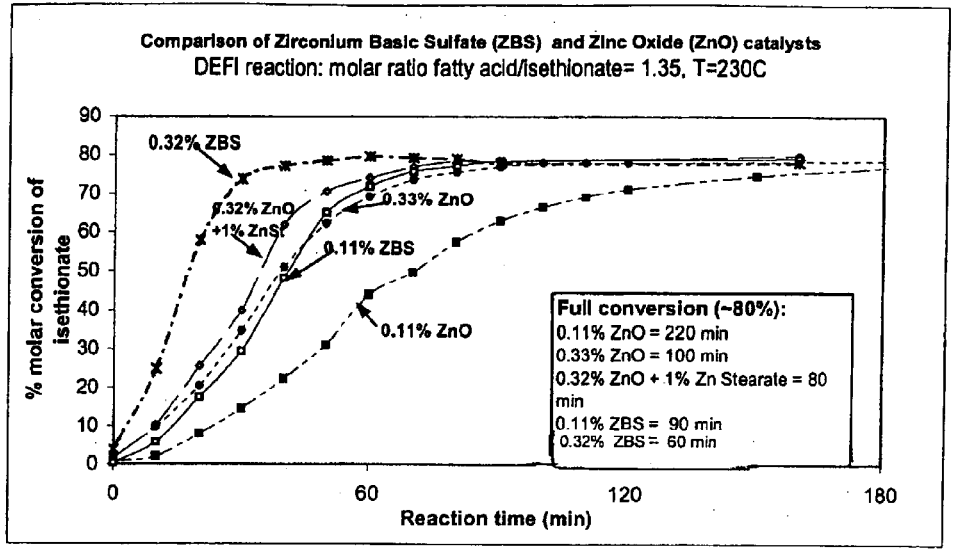
FIG. 1 graphs the reaction time and conversion rate of zirconium basic sulfate (ZBS) compared to zinc oxide (ZnO) or mixture of ZnO and zinc stearate. As seen, at about half the level (0.06 wt. % ZBS versus 0.11 wt. % ZnO), ZBS is far superior to ZnO (full conversion in 90 minutes versus 220 minutes at little more than half the level by weight).

The present invention relates to a process for producing directly esterifed fatty acyl isethionate (DEFI) wherein said process comprises reacting a fatty acid with alkali metal isethionate or ammonium isethionate in the presence of a catalyst comprising a Group 4 metal.

The catalyst accelerates reaction of the isethionate of formula HOR'SO$_3$M with fatty acid RCOOH (the DEFI reaction) to produce the directly esterified fatty acid isethionate of formula RCOOR'SO$_3$M where R, R' and M are as defined above.

In the reaction the molar ratio of fatty acid to isethionate may range from 1:1 to 2:1, preferably 1.2:1 to 1.5:1 and reactants are mixed at a temperature of about 190° C. to 255° C. It should be understood that this temperature range pertains to a reaction at atmospheric pressure and that, under vacuum, lower temperatures could be utilized.

Catalysts Compound

The catalysts which can be used according to the novel process of the invention are those comprising a Group 4 metal, e.g., catalysts comprising titanium, zirconium, hafnium or mixtures thereof. In preferred embodiments of the invention, the catalysts comprises zirconium. It should also be understood that the group 4 metals may be used in combination with other metals.

In one preferred embodiment, the catalyst is a zirconium salt. Among the zirconium salts which may be used are zirconium basic sulfate (i.e., zirconium oxide sulfate); zirconium basic carbonate; aluminum zirconium salts; or mixtures thereof. The aluminum-zirconium salts may comprise, for example, aluminum-zirconium tetrachlorohydrex glycine.

The catalysts could also be Group 4 metal alkoxides. Examples include titanium or zirconium alkoxide or mixtures thereof. Specific examples include zirconium ethoxide, zirconium propoxide, hafnium butoxide etc.

In one preferred embodiment, the catalyst comprises hydrated zirconium oxide.

While not wishing to be bound by theory, it is believed that the most preferred Group 4 catalysts are those meeting space and molecular weight specifications which enhance reaction mixture. Thus, for example, a background cluster of zirconium compounds (typically 5 to 10 Zr chain for example) is ideal for esterification. If molecular weight is too high, the catalyst may not be as effective and may precipitate out. A typical coordination number for Zr, for example, is 8, although coordination number of 10–12 is possible.

Again, while not wishing to be bound by theory, when the ideal bridged cluster chain is met, the mechanism for zirconium compounds (as an example) catalyzing esterification is believed to be as depicted below:

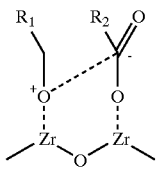

wherein fatty acid molecule (i.e., fatty acid molecule containing $R_2$ group attached to the group 4 metal based catalyst) isethionate molecule (i.e., isethionate molecule containing $R_1$ group attached to the group 4 metal based catalyst), and catalyst can link as shown to enhance reaction kinetics.

The fatty acid which contains the $R_2$ group can be $C_7$ to $C_{24}$ monocarboxylic fatty acids (saturated and/or unsaturated) and blends of these fatty acids.

While the molecules containing the R1 and R2 groups, respectively, are typically isethionate and fatty acid molecules, it should be understood that theoretically any esterification reaction can be enhanced using the catalyst of the invention.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. Further, all ranges are to be understood to encompass both the ends of the ranges plus all numbers subsumed within the ranges.

EXAMPLES

Example 1

In order to show the advantage of Group 4 metal based catalysts (either acting as sole catalysts or acting in cooperation with and other catalysts previously used in DEFI reaction) in the DEFI reaction (i.e., reaction combining isethionate salt and organic acid at about 190'–250° C. to produce directly esterified fatty acid isethionate of formula RCOOR'$SO_3$M as defined above), applicants compared the conversion rate into DEFI (Y axis) as a function of time based on the type and amount of catalyst used. Results are seen in FIG. 1. Specifically FIG. 1 shows the rate of conversion for 0.17% by wt. zirconium base sulfate (ZBS), for example, relative to 0.33 by wt. % zinc oxide. As clearly seen in the figure, ZBS produces a much higher conversion in much shorter time. Similarly, the ZBS full conversion (60 minutes as noted in the legend) was superior to a combination of 0.32% zinc oxide and 1% zinc stearate where, although far higher amounts of catalysts were used, full conversion was not achieved until 80 minutes.

Indeed, at one fifth to one sixth the amount of ZBS (0.06% ZBS versus 0.33% ZnO), the conversion rate of ZBS is almost the same as that for ZnO (90 minutes versus 100 minutes).

In short, it can be clearly seen that effectiveness of Group 4 metal based catalysts in DEFI reaction is superior to other catalysts on a molar % basis.

Example 2

Figure 2:
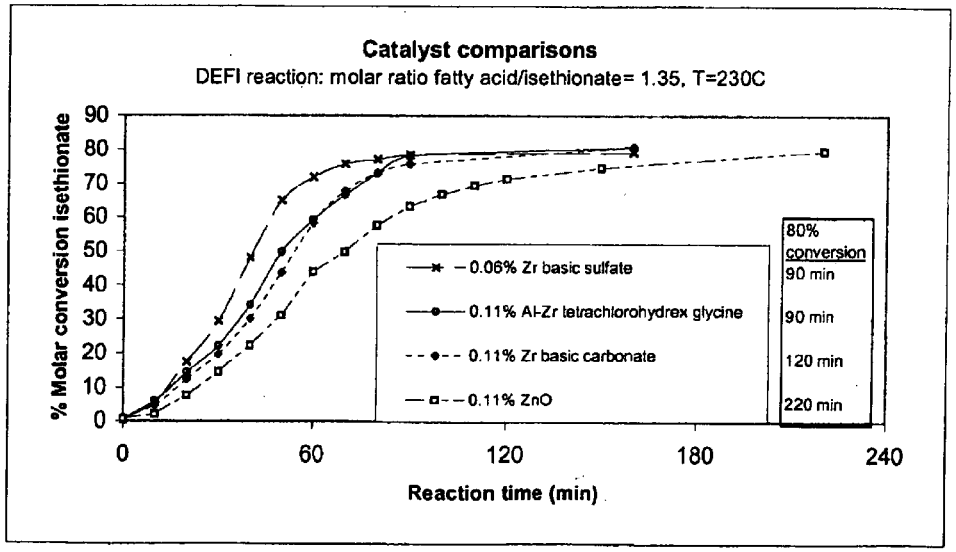
FIG. 2 is a comparison of rate and conversion percentage among various zirconium salts versus zinc oxide.

Applicants sought to compare different Group 4 metal based DEFI catalysts against one another as well as relative to well known zinc oxide (ZnO) DEFI catalysts and results are set forth in FIG. 2.

As seen in FIG. 2, on a wt. % to wt. % basis, zirconium basic carbonate, ZBS, and aluminum-zirconium salt were all superior to ZnO. ZBS was perhaps preferred catalyst with much better conversion at nearly half the amount (0.06% by wt. versus 0.11% by wt.).

Again, it can be seen that Group 4 metal based catalysts were superior to other known catalysts (e.g., ZnO) in DEFI reaction.

Example 3

Applicants also sought to demonstrate that in addition to zirconium based catalysts, other Group 4 metal based catalysts can be used, such as titanium and hafnium based catalysts. Also, in addition to using salts, Group 4 metal based alkoxides also prove to be quite effective catalysts.

Figure 3:
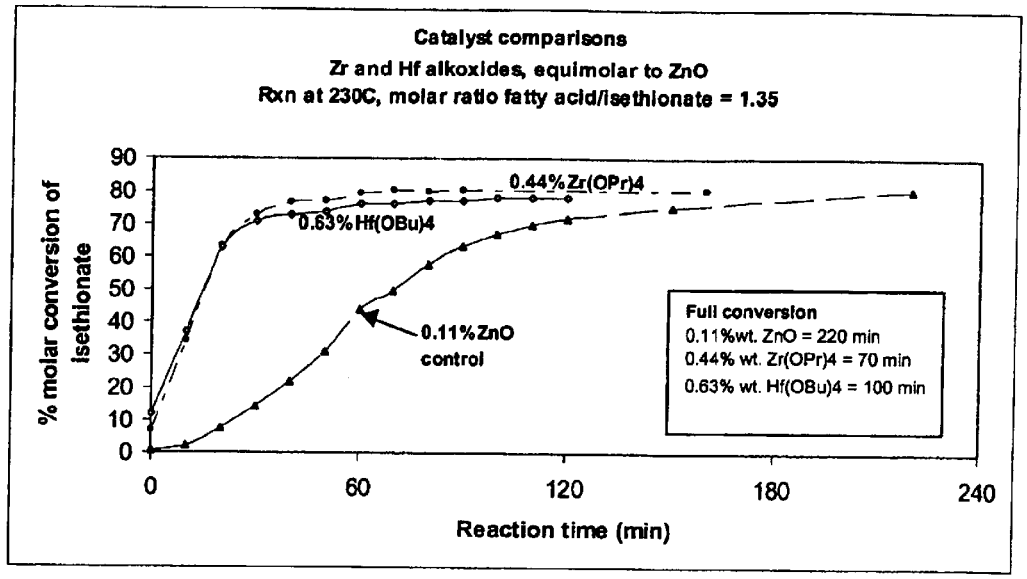
FIG. 3 shows that alkoxides of Group 4 metals, specifically zirconium propoxide and hafnium butoxide, are far more efficient than zinc oxide on an equimoar basis.

As seen in FIG. 3, on an equimolar comparison, zirconium propoxide, $Zr(OPr)_4$, and hafnium butoxide, $Hf(OBu)_4$, were superior to ZnO. $Zr(Opr)_4$, for example, showed much faster conversion times than ZnO (70 minutes versus 220 minutes).

Again, it can be seen that Group 4 metal based catalyst were superior to other known catalysts (e.g., ZnO) in DEFI reaction.

What is claimed is:

1. A process for producing directly esterified fatty acyl isethionate comprising reacting a fatty acid with an alkali metal isethionate or ammonium isethionate in the presence of a catalyst comprising a group 4 metal;
    wherein said group 4 metal is selected from the group consisting of titanium, hafnium, zirconium salt and mixtures thereof;
    wherein said zirconium salt is selected from the group consisting of zirconium oxide sulfate, zirconium base carbonate aluminum zirconium salt, zirconium oxide, zirconium alkoxide, hydrated zirconium oxide and mixtures thereof.

2. A process according to claim 1 comprising heating said fatty acid, isethionate and catalyst at about 190° C. to about 255° C. for sufficient time to produce directly esterified fatty acid isethionate.

3. A process according to claim 1 wherein said aluminum-zirconium salt comprises aluminum-zirconium tetrachlorohydroxy glycine.

4. A process according claim 1 wherein said catalyst comprises zirconium or hafnium alkoxide.

* * * * *